United States Patent
Buschmann et al.

(10) Patent No.: US 7,022,739 B2
(45) Date of Patent: Apr. 4, 2006

(54) SUBSTITUTED 1-AMINOBUTAN-3-OL COMPOUNDS

(75) Inventors: Helmut Buschmann, Aachen (DE); Corinna Maul, Aachen (DE); Bernd Sundermann, Aachen (DE); Utz-Peter Jagusch, Aachen (DE); Michael Haurand, Aachen (DE); Boris Chizh, Aachen (DE)

(73) Assignee: Gruenenthal GmbH, Aachen (DE)

( * ) Notice: Subject to any disclaimer, the term of this patent is extended or adjusted under 35 U.S.C. 154(b) by 160 days.

(21) Appl. No.: 10/401,020

(22) Filed: Mar. 28, 2003

(65) Prior Publication Data

US 2003/0216393 A1    Nov. 20, 2003

Related U.S. Application Data

(63) Continuation of application No. PCT/EP01/11231, filed on Sep. 28, 2001.

(30) Foreign Application Priority Data

Sep. 29, 2000  (DE) ................................ 100 49 483

(51) Int. Cl.
  *A61K 31/135*  (2006.01)
  *A61K 31/13*   (2006.01)
  *C07C 211/00*  (2006.01)

(52) U.S. Cl. ...................... 514/646; 514/659; 564/305; 564/455

(58) Field of Classification Search ................ 564/305, 564/455; 514/646, 659
See application file for complete search history.

(56) References Cited

U.S. PATENT DOCUMENTS

| 4,155,935 | A  |   | 5/1979  | Yardley et al. |         |
|-----------|----|---|---------|----------------|---------|
| 6,548,534 | B1 | * | 4/2003  | Lehmann et al. | 514/435 |
| 6,660,774 | B1 | * | 12/2003 | Christoph et al.| 514/646 |
| 6,673,794 | B1 | * | 1/2004  | Puetz et al.   | 514/239.5|
| 6,780,891 | B1 | * | 8/2004  | Senanayake et al.| 514/646 |

OTHER PUBLICATIONS

Kauffmann, et al. "Alkylchromium and alkylmanganese reagents. IV. The aldehyde-selective and cheleselective alkylation of organic carbonyl compounds with monoalkylchromium(III) reagents."
Moelm et al. "Fragmentation reactions of quaternized synthesis of highly functionalized oxetanes and unsaturated aldehydes and ketones with a (Z)-CC double bond."
International Search Report.

* cited by examiner

*Primary Examiner*—Deborah C. Lambkin
(74) *Attorney, Agent, or Firm*—Crowell & Moring LLP

(57) ABSTRACT

Substituted 1-aminobutane-3-ol compounds, methods for producing them, pharmaceutical compounds containing them, and the use of substituted 1-aminobutane-3-ol compounds for producing pharmaceutical compounds.

34 Claims, No Drawings

SUBSTITUTED 1-AMINOBUTAN-3-OL COMPOUNDS

CROSS REFERENCE TO RELATED APPLICATIONS

This application is a continuation of international patent application no. PCT/EP01/11231, filed Sep. 28, 2001, designating the United States of America, and published in German as WO 02/28817, the entire disclosure of which is incorporated herein by reference. Priority is claimed based on Federal Republic of Germany patent application no. DE 100 49 483.8, filed Sep. 29, 2000.

BACKGROUND OF THE INVENTION

The present invention relates to substituted 1-aminobutan-3-ol compounds, processes for their production, medicaments containing these compounds, and the use of substituted 1-aminobutan-3-ol compounds for the production of pharmaceutical compositions.

The cyclic GABA analogue gabapentin is a clinically proven antiepileptic. Gabapentin additionally exhibits further interesting, medically relevant properties, in particular as an analgesic. New classes of structures that have an affinity for the gabapentin binding site are therefore of interest. In connection with the aforementioned medical indications there is a further need for substances that are similar in their properties to gabapentin, for example as regards analgesic effect.

The treatment of chronic and non-chronic pain conditions is very important in medicine. There is therefore a wide need for highly effective pain treatments. The urgent need for a patient-oriented and targeted treatment of chronic and non-chronic pain conditions, which is understood to include the successful and satisfactory treatment of pain on the part of the patient, is documented in the large number of scientific studies that have recently appeared in the field of applied analgesia and in basic research relating to nociception.

Conventional opioids such as morphine are highly effective in treating severe to extremely severe pain. Their use is however limited by the known side effects such as for example respiratory depression, vomiting, sedation, constipation and development of tolerance. Also, they are less effective in treating neuropathic or incidental pain afflicting in particular tumour patients.

SUMMARY OF THE INVENTION

The object of the invention was accordingly to provide new compounds that have an affinity for the gabapentin binding site and/or corresponding physiological activities.

A particular object of the invention was to provide compounds which are effective analgesics.

The invention accordingly provides substituted 1-aminobutan-3-ol derivatives of the general formula I,

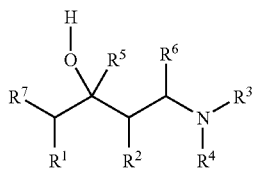

I wherein
R$^1$ and R$^2$ in each case independently of one another are selected from C$_{1-6}$-alkyl that is branched or unbranched, saturated or unsaturated, unsubstituted or singly or multiply substituted, or
R$^1$ and R$^2$ together form a (CH$_2$)$_{2-9}$ ring that may optionally be substituted with C$_{1-8}$-alkyl that is branched or unbranched, saturated or unsaturated, unsubstituted or singly or multiply substituted; or aryl that is unsubstituted or singly or multiply substituted,
R$^3$ and R$^4$ in each case independently of one another are selected from C$_{1-6}$-alkyl that is branched or unbranched, saturated or unsaturated, unsubstituted or singly or multiply substituted; C$_{3-6}$-cycloalkyl that is saturated or unsaturated, unsubstituted or singly or multiply substituted; phenyl, benzyl or phenethyl that is unsubstituted or singly or multiply substituted, or the radicals R$^3$ and R$^4$ together form a ring and denote CH$_2$CH$_2$OCH$_2$CH$_2$, CH$_2$CH$_2$NR$^{22}$CH$_2$CH$_2$ or (CH$_2$)$_{3-6}$
where R$^{22}$ is selected from H; C$_{1-10}$-alkyl or C$_{3-10}$-cycloalkyl, in each case saturated or unsaturated, branched or unbranched, singly or multiply substituted or unsubstituted; aryl or heteroaryl, in each case singly or multiply substituted or unsubstituted; or aryl, C$_{3-10}$-cycloalkyl or heteroaryl, in each case singly or multiply substituted or unsubstituted, and that is bound via C$_{1-3}$-alkyl that is saturated or unsaturated;
R$^5$ is selected from C$_{1-10}$-alkyl that is saturated or unsaturated, branched or unbranched, singly or multiply substituted or unsubstituted; saturated or unsaturated C$_{3-9}$-cycloalkyl; aryl, heteroaryl, aryl bound via saturated or unsaturated C$_{1-3}$-alkyl, C$_{3-10}$-cycloalkyl bound via saturated or unsaturated C$_{1-3}$-alkyl or heteroaryl bound via saturated or unsaturated C$_{1-3}$-alkyl, wherein all aryl, heteroaryl and cycloalkyl radicals may in each case independently of one another be unsubstituted or singly or multiply substituted with radicals selected independently of one another from
F, Cl, Br, I, OR$^{18}$, SR$^{18}$ SO$_2$R$^{18}$, SO$_2$OR$^{18}$, CN, COOR$_{18}$, NR$^{19}$R$^{20}$; C$_{1-10}$-alkyl that is saturated or unsaturated, branched or unbranched, singly or multiply substituted or unsubstituted; C$_{3-9}$-cycloalkyl that is saturated or unsaturated, unsubstituted or singly or multiply substituted;
aryl or heteroaryl, in each case unsubstituted or singly or multiply substituted; or aryl bound via saturated or unsaturated C$_{1-3}$-alkyl, C$_{3-9}$-cycloalkyl or heteroaryl, in each case unsubstituted or singly or multiply substituted;
where R$^{18}$ is selected from H; C$_{1-10}$-alkyl that is saturated or unsaturated, branched or unbranched, unsubstituted or singly or multiply substituted; C$_{3-9}$-cycloalkyl that is saturated or unsaturated, unsubstituted or singly or multiply substituted; aryl or heteroaryl that is unsubstituted or singly or multiply substituted; or aryl bound via saturated or unsaturated C$_{1-3}$-alkyl, C$_{3-9}$-cycloalkyl or heteroaryl, in each case unsubstituted or singly or multiply substituted;
R$^{19}$ and R$^{20}$ are selected independently of one another from H; C$_{1-10}$-alkyl that is saturated or unsaturated, branched or unbranched, unsubstituted or singly or multiply substituted; C$_{3-9}$-cycloalkyl that is saturated or unsaturated, unsubstituted or singly or multiply substituted; aryl or heteroaryl in each case unsubstituted or singly or multiply substituted; or aryl bound via saturated or unsaturated $C_{1-3}$-alkyl, $C_{3-9}$-cycloalkyl or heteroaryl, in each case unsubstituted or singly or multiply substituted; or $R^{19}$ and $R^{20}$ together form $CH_2CH_2OCH_2CH_2$, $CH_2CH_2NR^{21}CH_2CH_2$ or $(CH_2)_{3-6}$, where $R^{21}$ is selected from H, $C_{1-10}$-alkyl that is saturated or unsaturated, branched or unbranched, unsubstituted or singly or multiply substituted;

$R^6$ is selected from H; aryl or heteroaryl in each case unsubstituted or singly or multiply substituted; and $R^7$ is selected from halogen, $CF_3$; $C_{1-6}$-alkyl that is branched or unbranched, saturated or unsaturated, unsubstituted or singly or multiply substituted; $C_{3-9}$-cycloalkyl that is saturated or unsaturated, unsubstituted or singly or multiply substituted; aryl, heteroaryl that is in each case unsubstituted or singly or multiply substituted; aryl bound via saturated or unsaturated $C_{1-3}$-alkyl, $C_{3-9}$-cycloalkyl or heteroaryl, in each case unsubstituted or singly or multiply substituted optionally in the form of their racemates, their pure stereoisomers, in particular enantiomers or diastereomers, or in the form of mixtures of the stereoisomers, in particular of the enantiomers or diastereomers, in an arbitrary mixture ratio; in the illustrated form or in the form of their acids or their bases, or in the form of their salts, in particular the physiologically acceptable salts, or in the form of their solvates, in particular the hydrates.

The substances according to the invention bind to the gabapentin binding site and exhibit an excellent analgesic action.

Within the scope of the present invention, alkyl radicals and cycloalkyl radicals are understood to include saturated and unsaturated (but not aromatic), branched, unbranched and cyclic hydrocarbons that may be unsubstituted or singly or multiply substituted. In this regard, $C_{1-2}$-alkyl denotes C1- or C2-alkyl, $C_{1-3}$-alkyl denotes C1-, C2- or C3-alkyl, $C_{1-4}$-alkyl denotes C1-, C2-, C3- or C4-alkyl, $C_{1-5}$-alkyl denotes C1-, C2-, C3-, C4- or C5-alkyl, $C_{1-6}$-alkyl denotes C1-, C2-, C3-, C4-, C5- or C6-alkyl, $C_{1-7}$-alkyl denotes C1-, C2-, C3-, C4-, C5-, C6- or C7-alkyl, $C_{1-8}$-alkyl denotes C1-, C2-, C3-, C4-, C5-, C6-, C7- or C8-alkyl, $C_{1-10}$-alkyl denotes C1-, C2-, C3-, C4-, C5-, C6-, C7-, C8-, C9- or C10-alkyl and $C_{1-18}$-alkyl denotes C1-, C2-, C3-, C4-, C5-, C6-, C7-, C8-, C9-, C10-, C11-, C12-, C13-, C14-, C15-, C16-, C17- or C18-alkyl. In addition $C_{3-4}$-cycloalkyl denotes C3- or C4-cycloalkyl, $C_{3-5}$-cycloalkyl denotes C3-, C4- or C5-cycloalkyl, $C_{3-6}$-cycloalkyl denotes C3-, C4-, C5- or C6-cycloalkyl, $C_{3-7}$-cycloalkyl denotes C3-, C4-, C5-, C6- or C7-cycloalkyl, $C_{3-8}$-cycloalkyl denotes C3-, C4-, C5-, C6-, C7- or C8-cycloalkyl, $C_{4-5}$-cycloalkyl denotes C4- or C5-cycloalkyl, $C_{4-6}$-cycloalkyl denotes C4-, C5- or C6-cycloalkyl, $C_{4-7}$-cycloalkyl denotes C4-, C5-, C6- or C7-cycloalkyl, $C_{5-6}$-cycloalkyl denotes C5- or C6-cycloalkyl and $C_{5-7}$-cycloalkyl denotes C5-, C6- or C7-cycloalkyl. With regard to cycloalkyl, the term also includes saturated cycloalkyls in which 1 or 2 carbon atoms are replaced by a heteroatom, i.e. S, N or O. The term cycloalkyl however also includes in particular singly or multiply, preferably singly, unsaturated cycloalkyls without a heteroatom in the ring as long as the cycloalkyl does not form an aromatic system. The alkyl or cycloalkyl radicals are preferably methyl, ethyl, vinyl -(ethenyl), propyl, allyl(2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, but also adamantyl, $CHF_2$, $CF_3$ or $CH_2OH$ as well as pyrazolinone, oxopyrazolinone, [1,4]dioxane or dioxolane.

In connection with alkyl and cycloalkyl—unless expressly defined otherwise—the term substituted within the context of the present invention is understood to mean the substitution of at least one (optionally also several) hydrogen atom(s) by F, Cl, Br, I, $NH_2$, SH or OH, and the term "multiply substituted" or "substituted" in the case of multiple substitution is understood to mean that the substitution takes place on different as well as on the same atoms multiply with the same or different substituents, for example triply on the same C atom as in the case of $CF_3$ or at different positions as in the case of $—CH(OH)—CH=CH—CHCl_2$. Particularly preferred substituents in this connection are F, Cl and OH. With regard to cycloalkyl, the hydrogen atom may also be replaced by $OC_{1-3}$-alkyl or $C_{1-3}$-alkyl (in each case singly or multiply substituted or unsubstituted), in particular methyl, ethyl, n-propyl, i-propyl, $CF_3$, methoxy or ethoxy.

The term $(CH_2)_{3-6}$ is understood to denote $—CH_2—CH_2—CH_2—$, $—CH_2—CH_2—CH_2—CH_2—$, $—CH_2—CH_2—CH_2—CH_2—CH_2—$, and $—CH_2—CH_2—CH_2—CH_2—CH_2—CH_2—$, and the term $(CH_2)_{1-4}$ is understood to denote $—CH_2—$, $—CH_2—CH_2—$, $—CH_2—CH_2—CH_2—$ and $—CH_2—CH_2—CH_2—CH_2—$, etc.

The term aryl radical is understood to mean ring systems with at least one aromatic ring but without heteroatoms in also only one of the rings. Examples are phenyl, naphthyl, fluoranthenyl, fluorenyl, tetralinyl or indanyl, in particular 9H-fluorenyl or anthracenyl radicals, which may be unsubstituted or singly or multiply substituted.

The term heteroaryl radical is understood to mean heterocyclic ring systems with at least one unsaturated ring, which contain one or more heteroatoms from the group comprising nitrogen, oxygen and/or sulfur, and which may also be singly or multiply substituted. Examples of the group of heteroaryls that may be mentioned include furan, benzofuran, thiophene, benzothiophene, pyrrole, pyridine, pyrimidine, pyrazine, quinoline, isoquinoline, phthalazine, benzo[1,2,5]thiadiazole, benzothiazole, indole, benzotriazole, benzodioxolane, benzodioxane, carbazole, indole and quinazoline.

In this connection the term substituted in connection with aryl and heteroaryl is understood—unless otherwise specifically defined—to denote the substitution of the aryl or heteroaryl with $R^{23}$, $OR^{23}$, a halogen, preferably F and/or Cl, a $CF_3$, a CN, an $NO_2$, an $NR^{24}R^{25}$, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene.

In this connection the radical $R^{23}$ denotes H, a $C_{1-10}$-alkyl radical, preferably a $C_{1-6}$-alkyl radical, an aryl or heteroaryl radical or an aryl or heteroaryl radical bonded via saturated or unsaturated $C_{1-3}$-alkyl or via a $C_{1-3}$-alkylene group, wherein these aryl and heteroaryl radicals may not themselves be substituted by aryl or heteroaryl radicals; the radicals $R^{24}$ and $R^{25}$, which are identical or different, denote H, a $C_{1-10}$-alkyl radical, preferably a $C_{1-6}$-alkyl radical, an aryl radical, a heteroaryl radical or an aryl or heteroaryl radical bonded via saturated or unsaturated $C_{1-3}$-alkyl or via a $C_{1-3}$-alkylene group, wherein these aryl and heteroaryl radicals may not themselves be substituted by aryl or heteroaryl radicals, or the radicals $R^{24}$ and $R^{25}$ together denote $CH_2CH_2OCH_2CH_2$, $CH_2CH_2NR^{26}CH_2CH_2$, or $(CH_2)_{3-6}$, and the radical $R^{26}$ denotes H, a $C_{1-10}$-alkyl radical, preferably a $C_{1-6}$-alkyl radical, an aryl or heteroaryl radical, or an aryl or heteroaryl radical bonded via saturated or unsaturated $C_{1-3}$-alkyl or via a $C_{1-3}$-alkylene group, wherein these aryl and heteroaryl radicals may not themselves be substituted with aryl or heteroaryl radicals.

The term salt is understood to mean any form of the active constituent according to the invention in which this adopts an ionic form or is charged and is coupled to a counterion (a cation or anion), and is present in solution. The term is also understood to include complexes of the active constituent with other molecules and ions, in particular complexes that are complexed via ionic interactions. In particular the term salt is understood to mean physiologically acceptable salts with cations or bases and physiologically acceptable salts with anions or acids.

The term physiologically acceptable salt with cations or bases is understood within the context of the present invention to mean salts of at least one of the compounds according to the invention—generally of a (deprotonated) acid—as an anion with at least one, preferably inorganic cation, that are physiological acceptable, especially when used in humans and/or mammals. Particularly preferred are the salts of alkali and alkaline earth metals, but also with $NH_4^+$, and in particular (mono) or (di)sodium, (mono) or (di)potassium, magnesium or calcium salts.

The term physiologically acceptable salt with anions or acids is understood within the context of the present invention to mean salts of at least one of the compounds according to the invention—generally protonated, for example on the nitrogen atom—as a cation with at least one anion, that are physiologically acceptable, especially when used in humans and/or mammals. In the context of the present invention the term is particularly understood to denote the salt formed with a physiologically acceptable acid, namely salts of the respective active constituent with inorganic or organic acids, that are physiologically acceptable, especially when used in humans and/or mammals. Examples of physiologically acceptable salts of specific acids are salts of: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydrol$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The hydrochloride salt is particularly preferred.

In a preferred embodiment of the invention, in the substituted 1-aminobutan-3-ol derivatives according to the invention of the formula I $R^6$ is selected from H or heteroaryl or is preferably a radical according to formula II

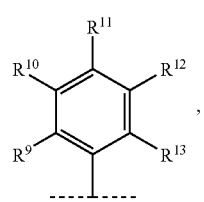

II where $R^9$ to $R^{13}$ in each case independently of one another are selected from H, F, Cl, Br, I, $CF_3$, OH, $OR^{14}$, $OCF_3$, $SR^{14}$, $SO_2CH_3$, $SO_2CF_3$; $C_{1-6}$-alkyl that is branched or unbranched, saturated or unsaturated, unsubstituted or singly or multiply substituted; phenyl that is unsubstituted or singly or multiply substituted; CN, $COOR^{14}$, $NO_2$ or wherein $R^9$ and $R^{10}$ or $R^{10}$ and $R^{11}$ together form an $OCH_2O$ or $OCH_2CH_2O$ ring, and $R^{14}$ is selected from $C_{1-6}$-alkyl that is branched or unbranched, saturated or unsaturated, unsubstituted or singly or multiply substituted;

phenyl, benzyl, phenethyl or thiophenyl, in each case unsubstituted or singly or multiply substituted.

In a further, but particularly preferred embodiment of the invention, in the substituted 1-aminobutan-3-ol derivatives according to the invention of the formula I $R^1$ and $R^2$ together form a $(CH_2)_{2-5}$ ring that may optionally be substituted by $C_{1-6}$-alkyl that is branched or unbranched, saturated or unsaturated, unsubstituted or singly or multiply substituted; or phenyl that is unsubstituted or singly or multiply substituted; but is preferably unsubstituted.

In another preferred embodiment of the invention, in the substituted 1-aminobutan-3-ol derivatives according to the invention of the formula I $R^3$ and $R^4$ in each case independently of one another are selected from $C_{1-6}$-alkyl that is branched or unbranched, saturated or unsaturated, unsubstituted or singly or multiply substituted.

Preferably both denote $CH_3$;

or the radicals $R^3$ and $R^4$ together form a ring and denote $CH_2CH_2NR^{22}CH_2CH_2$ or $(CH_2)_{3-6}$, and in particular together denote $(CH_2)_{4-5}$ or $CH_2CH_2NR_{22}CH_2CH_2$ where $R^{22}$ is selected from H or $C_{1-6}$-alkyl that is saturated, branched or unbranched and unsubstituted; in particular H or $CH_3$.

In a preferred embodiment of the invention, in the substituted 1-aminobutan-3-ol derivatives according to the invention of the formula I $R^5$ is selected from $C_{1-6}$-alkyl that is saturated or unsaturated, branched or unbranched, singly or multiply substituted or unsubstituted; $C_{5-6}$-cycloalkyl, phenyl, thiophenyl, furyl, benzofuranyl, benzothiophenyl, pyrrolyl, pyridinyl, pyrimidinyl, quinolinyl, isoquinolinyl, quinazolinyl, phenyl bonded via saturated or unsaturated $C_{1-3}$-alkyl, $C_{5-6}$-cycloalkyl bonded via saturated or unsaturated $C_{1-3}$-alkyl, or thiophenyl, furyl, benzofuranyl, bonzothiophenyl, pyrrolyl, pyridinyl, pyrimidinyl, quinolinyl, isoquinolinyl, quinazolinyl bonded via saturated or unsaturated $C_{1-3}$-alkyl, wherein all aryl, heteroaryl and cycloalkyl radicals may in each case independently of one another be unsubstituted or singly or multiply substituted;

preferably $R^5$ is selected from phenyl or thiophenyl that is unsubstituted or singly or multiply substituted, preferably with F, Cl, Br, I, OH, O—$C_{1-4}$-alkyl, $C_{1-6}$-alkyl, $NH_2$ and/or SH; or phenyl bonded via saturated or unsaturated $C_{1-3}$-alkyl and that is unsubstituted or singly or multiply substituted, preferably with F, Cl, Br, I, OH, O—$C_{1-4}$-alkyl, $C_{1-6}$-alkyl, $NH_2$ and/or SH;

in particular $R^5$ is selected from phenyl that is unsubstituted or singly or multiply substituted, preferably with F, Cl, Br, I, OH, $OCH_3$, $OC_2H_5$, $OC_3H_7$, SH, $CH_3$, $C_2H_5$, $C_3H_7$ and/or $C_4H_9$.

Overall it is preferred with regard to the substituent $R^5$ that if $R^5$ is selected from aryl, heteroaryl or cycloalkyl that is directly bonded or bonded via saturated or unsaturated $C_{1-3}$-alkyl, then these are singly or multiply substituted or unsubstituted, preferably with radicals selected independently of one another from F, Cl, Br, I, $OR^{18}$, $SR^{18}$, $COOR^{18}$, $NH_2$; $C_{1-10}$-alkyl that is saturated or unsaturated, branched or unbranched, singly or multiply substituted or unsubstituted;

where $R^{18}$ is selected from H; $C_{1-6}$-alkyl that is saturated or unsaturated, branched or unbranched, unsubstituted or singly or multiply substituted;

in particular with radicals that are selected independently of one another from

F, Cl, Br, I, OH, O—$C_{1-4}$-alkyl, $C_{1-6}$-alkyl, $NH_2$ and/or SH.

In yet a further preferred embodiment of the invention, in the substituted 1-aminobutan-3-ol derivatives according to the invention of the formula I $R^7$ is selected from $C_{1-6}$-alkyl that is branched or unbranched, saturated or unsaturated, unsubstituted or singly or multiply substituted;

$C_{5-7}$-cycloalkyl that is saturated or unsaturated, unsubstituted or singly or multiply substituted, preferably cyclohexyl; phenyl that is unsubstituted or singly or multiply substituted;

phenyl that is bonded via saturated or unsaturated $C_{1-3}$-alkyl, in each case unsubstituted or singly or multiply substituted, preferably $R^7$ is selected from phenyl that is unsubstituted or singly or multiply substituted;

phenyl bonded via saturated or unsaturated $C_{1-3}$-alkyl, in each case unsubstituted or singly or multiply substituted.

In another preferred embodiment of the invention, in the substituted 1-aminobutan-3-ol derivatives according to the invention of the formula I, if $R^5$ and/or $R^7$ is/are selected from aryl, $C_{3-9}$-cycloalkyl or heteroaryl bound via saturated or unsaturated $C_{1-3}$-alkyl, then the $C_{1-3}$-alkyl bonded via the aryl, heteroaryl or cycloalkyl is selected from:

—$CH_2$—, —$C_2H_4$—, —$C_3H_6$—, —C≡C—, —CH=CH—, —CH=CH—$CH_2$—, —$CH_2$—CH=CH—, —C≡C—$CH_2$— or —$CH_2$—C≡C—, preferably —$CH_2$—, —$C_2H_4$— or —C≡C—.

In another preferred embodiment of the invention the substituted 1-aminobutan-3-ol derivatives according to the invention are selected from the following group:

2-benzyl-1-(2,4-dichlorobenzyl)-6-dimethylaminomethylcyclohexanol
2-benzyl-1-(3-chlorobenzyl)-6-dimethylaminomethylcyclohexanol
2-benzyl-6-dimethylaminomethyl-1-(2,5-dimethylbenzyl)-cyclohexanol
2-benzyl-1-(2-chloro-6-fluorobenzyl)-6-dimethylaminomethylcyclohexanol
2-benzyl-1-(4-chlorobenzyl)-6-dimethylaminomethylcyclohexanol
2-benzyl-6-dimethylaminomethyl-1-(3-trifluoromethylphenyl)-cyclohexanol
2-benzyl-6-dimethylaminomethyl-1-(2-methylbenzyl)-cyclohexanol
2-benzyl-6-dimethylaminomethyl-1-(2-methoxyphenyl)-cyclohexanol
2-benzyl-1-(4-chloro-3-trifluoromethylphenyl)-6-dimethylaminomethylcyclohexanol
2-benzyl-1-(2-chlorobenzyl)-6-dimethylaminomethylcyclohexanol
2-benzyl-1-(3,5-dichlorophenyl)-6-dimethylaminomethylcyclohexanol
2-benzyl-1-(3-chlorophenyl)-6-dimethylaminomethylcyclohexanol
2-benzyl-6-dimethylaminomethyl-1-(3-fluorophenyl)-cyclohexanol
2-benzyl-6-dimethylaminomethyl-1-(5-fluoro-2-methoxyphenyl)-cyclohexanol
2-benzyl-1-cyclohexylmethyl-6-dimethylaminomethylcyclohexanol
2-benzyl-6-dimethylaminomethyl-1-(4-methoxyphenyl)-cyclohexanol
2-benzyl-6-dimethylaminomethyl-1-p-tolylcyclohexanol
2-benzyl-6-dimethylaminomethyl-1-(3-phenylpropyl)-cyclohexanol
2-benzyl-6-dimethylaminomethyl-1-(3-methoxyphenyl)-cyclohexanol
2-benzyl-6-dimethylaminomethyl-1-thiophen-2-yl-cyclohexanol
2-benzyl-6-dimethylaminomethyl-1-phenylethynylcyclohexanol
2-benzyl-6-dimethylaminomethyl-1-(4-fluorophenyl)-cyclohexanol
2-benzyl-6-dimethylaminomethylbicyclohexyl-1-ol
2-benzyl-6-dimethylaminomethyl-1-m-tolylcyclohexanol
2-benzyl-1-(4-tert.-butylphenyl)-6-dimethylaminomethylcyclohexanol
2-benzyl-6-dimethylaminomethyl-1-vinylcyclohexanol
2-benzyl-6-dimethylaminomethyl-1-o-tolylcyclohexanol
2-benzyl-6-dimethylaminomethyl-1-(4-fluoro-3-methylphenyl)-cyclohexanol
1,2-dibenzyl-6-dimethylaminomethylcyclohexanol
2-benzyl-1-(4-chlorophenyl)-6-dimethylaminomethylcyclohexanol
2-benzyl-6-dimethylaminomethyl-1-phenylcyclohexanol
2-dimethylaminomethyl-1-(2,5-dimethylphenyl)-6-(3-methoxyphenyl)-cyclohexanol
1-cyclohexylmethyl-2-dimethylaminomethyl-6-(3-methoxyphenyl)-cyclohexanol
1-(2,4-dichlorobenzyl)-2-dimethylaminomethyl-6-(3-methoxyphenyl)-cyclohexanol
2-dimethylaminomethyl-6-(3-methoxyphenyl)-1-phenylethynylcyclohexanol
2-dimethylaminomethyl-6-(3-methoxyphenyl)-1-o-tolylcyclohexanol
1-(4-chlorophenyl)-2-dimethylaminomethyl-6-(3-methoxyphenyl)-cyclohexanol
2-dimethylaminomethyl-1-(3-fluorophenyl)-6-(3-methoxyphenyl)-cyclohexanol
2-dimethylaminomethyl-1-(3-fluoro-4-methoxyphenyl)-6-(3-methoxyphenyl)-cyclohexanol
1-(3-chlorobenzyl)-2-dimethylaminomethyl-6-(3-methoxyphenyl)-cyclohexanol
2-dimethylaminomethyl-1-(3-methoxybenzyl)-6-(3-methoxyphenyl)-cyclohexanol
1-(4-chloro-3-trifluoromethylphenyl)-2-dimethylaminomethyl-6-(3-methoxyphenyl)-cyclohexanol
1-(3,5-dichlorobenzyl)-2-dimethylaminomethyl-6-(3-methoxyphenyl)-cyclohexanol
2-dimethylaminomethyl-6-(3-methoxyphenyl)-1-phenylethynylcyclohexanol
1-(4-chlorophenyl)-2-dimethylaminomethyl-6-(3-methoxyphenyl)-cyclohexanol
2-dimethylaminomethyl-6-(3-methoxyphenyl)-1-o-tolylcyclohexanol
1-(3-chlorobenzyl)-2-dimethylaminomethyl-6-methylcyclohexanol
2-dimethylaminomethyl-1-(2,5-dimethylbenzyl)-6-methylcyclohexanol
1-(2-chloro-6-fluorobenzyl)-2-dimethylaminomethyl-6-methylcyclohexanol 1-(4-chlorobenzyl)-2-dimethylaminomethyl-6-methylcyclohexanol
2-dimethylaminomethyl-6-methyl-1-(3-methylbenzyl)-cyclohexanol
2-dimethylaminomethyl-6-methyl-1-(3-trifluoromethylphenyl)-cyclohexanol
1-(2-chloro-3-fluorophenyl)-2-dimethylaminomethyl-6-methylcyclohexanol
2-dimethylaminomethyl-6-methyl-1-(2-methylbenzyl)-cyclohexanol
2-dimethylaminomethyl-1-(2-methoxyphenyl)-6-methylcyclohexanol
2-dimethylaminomethyl-1-(3-fluorobenzyl)-6-methylcyclohexanol
2-dimethylaminomethyl-1-(4-fluorobenzyl)-6-methylcyclohexanol
1-(2-chlorobenzyl)-2-dimethylaminomethyl-6-methylcyclohexanol
1-(3,5-dichlorophenyl)-2-dimethylaminomethyl-6-methylcyclohexanol
1-(3-chlorophenyl)-2-dimethylaminomethyl-6-methylcyclohexanol
2-dimethylaminomethyl-1-(3-fluorophenyl)-6-methylcyclohexanol
2-dimethylaminomethyl-1-(3-fluoro-4-methoxyphenyl)-6-methylcyclohexanol
2-dimethylaminomethyl-1-(4-methoxyphenyl)-6-methylcyclohexanol
2-dimethylaminomethyl-6-methyl-1-p-tolylcyclohexanol
2-dimethylaminomethyl-6-methyl-1-(3-phenylpropyl)-cyclohexanol
2-dimethylaminomethyl-1-(3-methoxyphenyl)-6-methylcyclohexanol
2-dimethylaminomethyl-6-methyl-1-thiophen-2-yl-cyclohexanol
2-dimethylaminomethyl-6-methyl-1-phenylethynylcyclohexanol
2-dimethylaminomethyl-6-methyl-1-phenethylcyclohexanol
2-dimethylaminomethyl-1-(4-fluorophenyl)-6-methylcyclohexanol
1-(3-chlorobenzyl)-2-dimethylaminomethyl-6-(3-methoxyphenyl)-cyclohexanol
2-dimethylaminomethyl-1-(4-fluoro-2-methoxyphenyl)-6-(3-methoxyphenyl)-cyclohexanol
2-dimethylaminomethyl-1-(2-methoxyphenyl)-6-(3-methoxyphenyl)-cyclohexanol
2-dimethylaminomethyl-1-(4-fluorobenzyl)-6-(3-methoxyphenyl)-cyclohexanol
1-(3-chlorophenyl)-2-dimethylaminomethyl-6-(3-methoxyphenyl)-cyclohexanol
2-dimethylaminomethyl-6-(3-methoxyphenyl)-1-p-tolylcyclohexanol
2-dimethylaminomethyl-6-(3-methoxyphenyl)-1-(3-phenylpropyl)-cyclohexanol
2-dimethylaminomethyl-1,6-bis-(3-methoxyphenyl)-cyclohexanol
2-dimethylaminomethyl-6-(3-methoxyphenyl)-1-thiophen-2-yl-cyclohexanol
2-dimethylaminomethyl-6-(3-methoxyphenyl)-1-phenethylcyclohexanol
3-[3-dimethylaminomethyl-2-(4-fluorophenyl)-2-hydroxycyclohexyl]-phenol
3-(3-dimethylaminomethyl-2-hydroxy-2-phenylcyclohexyl)-phenol
3-[2-(4-tert.-butylphenyl)-3-dimethylaminomethyl-2-hydroxycyclohexyl]phenol
3-(3-dimethylaminomethyl-2-hydroxy-2-vinylcyclohexyl)-phenol
1-(4-chlorophenyl)-2-dimethylaminomethyl-6-(3-methoxyphenyl)-cyclohexanol
3-dimethylaminomethyl-2-(3-methoxyphenyl)-bicyclohexyl-2-ol
2-benzyl-6-dimethylaminomethyl-1-(4-trifluoromethylphenyl)-cyclohexanol
3-(2-benzyl-6-dimethylaminomethyl-1-hydroxycyclohexyl)-phenol
3-(2-tert.-butyl-6-dimethylaminomethyl-1-hydroxycyclohexyl)-phenol optionally in the form of their racemates, their pure stereoisomers, in particular enantiomers or diastereomers, or in the form of mixtures of the stereoisomers, in particular of the enantiomers or diastereomers, in an arbitrary mixture ratio; in the represented form or in the form of their acids or their bases or in the form of their salts, in particular of the physiologically acceptable salts, or in the form of their solvates, in particular the hydrates, especially the hydrochloride salts.

The substances according to the invention are toxicologically harmless, with the result that they are suitable for use as a pharmaceutical active constituent in medicaments. The invention therefore also provides medicaments containing at least one substituted 1-aminobutan-3-ol derivative according to the invention, as well as optionally suitable additives and/or auxiliary substances and/or optionally further active constituents.

The medicaments according to the invention contain, apart from at least one substituted 1-aminobutan-3-ol derivative according to the invention, optionally suitable additives and/or auxiliary substances, i.e. also carrier materials, fillers, solvents, diluents, dyes and/or binders, and may be administered as liquid medicament forms in the form of injection solutions, droplets or juices, or as semi-solid medicament forms in the form of granules, tablets, pellets, patches, capsules, plasters or aerosols. The choice of the auxiliary substances, etc., as well as the amounts thereof to be used depend on whether the medicament is to be administered orally, perorally, parenterally, intravenously, intraperitoneally, intradermally, intramuscularly, intranasally, buccally, rectally or topically, for example to the skin, the mucous membranes or the eyes. For oral administration, preparations in the form of tablets, sugar-coated pills, capsules, granules, drops, juices and syrups are suitable, while for parenteral, topical and inhalative application, solutions, suspensions, readily reconstitutable dry preparations as well as sprays are suitable. 1-aminobutan-3-ol derivatives according to the invention in a depôt form, in dissolved form or in a plaster, optionally with the addition of agents promoting skin penetration, are suitable percutaneous application preparations. Orally or percutaneously usable preparation forms may provide for a delayed release of the substituted 1-aminobutan-3-ol derivatives according to the invention. In principle further active constituents known to the person skilled in the art may be added to the medicaments according to the invention.

The amount of active constituent to be administered to the patient varies depending on the patient's weight, type of application, medical indication for use and the severity of the condition. Normally 0.005 to 1000 mg/kg, preferably 0.05 to 5 mg/kg of at least one substituted 1-aminobutan-3-ol derivative according to the invention are applied.

In a preferred form of the medicament, a contained substituted 1-aminobutan-3-ol derivative according to the invention is present as a pure diastereomer and/or enantiomer, as a racemate, or as a non-equimolar or equimolar mixture of the diastereomers and/or enantiomers.

Gabapentin is a known antiepileptic having an anticonvulsive action. In addition to this gabapentin is also used in various other medical conditions, and inter alia is prescribed by physicians for the treatment of migraine and bipolar disorders as well as hot flashes (e.g. in the post menopause) (M. Schrope, Modern Drug Discovery, September 2000, p. 11). Other medical conditions in which gabapentin exhibits a therapeutic potential have been identified in human studies and in clinical practice (J. S. Bryans, D. J. Wustrow; "3-Substituted GABA Analogs with Central Nervous System Activity: A Review" in Med. Res. Rev. (1999), pp. 149–177). The action of gabapentin is listed in detail in this review article. For example, gabapentin is effective in the treatment of chronic pain and behavioural disturbances. In particular the following properties of gabapentin are listed: anticonvulsive and antiepileptic actions, the use to treat chronic, neuropathic pain, in particular thermal hyperalgesia, mechanical allodynia, and cold-induced allodynia. In addition gabapentin is effective against neuropathy triggered by nerve damage, and in particular is also successful in treating neuropathic pain as well as inflammatory and post-operative pain. Gabapentin is also successful as an antipsychotic agent, in particular as an anxiolytic. Further proven indications for use include: amyotrophic lateral sclerosis (ALS), reflex sympathetic dystrophy (RSD), spastic paralysis, restless leg syndrome, treatment of symptoms and pain caused by multiple sclerosis, acquired nystagmus, treatment of the symptoms of Parkinson's disease, painful diabetic neuropathy and psychiatric disorders, for example bipolar disorders, mood fluctuations, manic behaviour. Gabapentin has also been successfully used to treat erythromelalgic pain, post-poliomyelitic pain, trigeminal neuralgia and post-herpetic neuralgia (Bryans and Wustrow (1999), etc.). The general efficacy of gabapentin in neurodegenerative conditions is widely known and is also demonstrated by the examples given in the aforementioned review article. Such neurodegenerative conditions include for example Alzheimer's disease, Huntington's disease, Parkinson's disease and epilepsy. The effectiveness of gabapentin in gastrointestinal disorders is also known.

All substances according to the invention displace gabapentin from its binding site, which has also not yet been experimentally determined. This implies however that the substances according to the invention bind at the same binding site and act physiologically via the latter, presumably with the same action profile as gabapentin. This assumption that the same action is also exerted at the same binding site is demonstrated by the analgesic effect. Thus, the compounds according to the invention not only displace gabapentin from its binding site but—like gabapentin—also have a marked analgesic effect.

The invention therefore also provides for the use of a substituted 1-aminobutan-3-ol derivative according to the invention for the production of a medicament for the treatment of pain, in particular neuropathic, chronic or acute pain.

The substances according to the invention may also be used to treat in particular symptoms associated with neuropathic pain as well as other related medical indications. The invention therefore also provides for the use of a substituted 1-aminobutan-3-ol derivative according to the invention for the production of a medicament for treating migraine, hyperalgesia and allodynia, in particular thermal hyperalgesia, mechanical hyperalgesia and allodynia and cold-induced allodynia, or inflammatory or post-operative pain.

The compounds according to the invention may also be used in other medical conditions. The invention accordingly furthermore provides for the use of a substituted 1-aminobutan-3-ol derivative according to the invention for the production of a medicament for treating epilepsy, hot flushes, post-menopausal symptoms, amyotropic lateral sclerosis (ALS), reflex sympathetic dystrophy (RSD), spastic paralysis, restless leg syndrome, acquired nystagmus; psychiatric or neuropathological disorders such as bipolar disorders, anxiety, panic attacks, mood fluctuations, manic behaviour, depression, manic-depressive behaviour; painful diabetic neuropathy, symptoms and pain due to multiple sclerosis or Parkinson's disease, neurodegenerative diseases such as Alzheimer's disease, Huntington's disease, Parkinson's disease and epilepsy; gastrointestinal lesions; erythromelalgic or post-poliomyelitic pain, trigeminal or post-herpetic neuralgia; or as an anticonvulsant, analgesic or anxiolytic.

In this connection it may be preferred if a used substituted 1-aminobutan-3-ol derivative according to one of claims 1 to 11 is present as a pure diastereomer and/or enantiomer, as a racemate, or as a non-equimolar or equimolar mixture of the diastereomers and/or enantiomers.

The invention also provides a process for treating a person or non-human mammal that requires treatment of medically relevant symptoms by administration of a therapeutically effective dose of a substituted 1-aminobutan-3-ol derivative according to the invention or a medicament according to the invention. The invention relates in particular to suitable processes for treating pain, in particular neuropathic, chronic or acute pain; migraine, hyperalgesia and allodynia, especially thermal hyperalgesia, mechanical hyperalgesia and allodynia and cold-induced allodynia, or for treating inflammatory or post-operative pain, epilepsy, hot flushes, post-menopausal symptoms, amyotropic lateral sclerosis (ALS), reflex sympathetic dystrophy (RSD), spastic paralysis, restless leg syndrome, acquired nystagmus; psychiatric or neuropathological disorders such as bipolar disorders, anxiety, panic attacks, mood fluctuations, manic behaviour, depression, manic-depressive behaviour; painful diabetic neuropathy, symptoms and pain due to multiple sclerosis or Parkinson's disease, neurodegenerative diseases such as Alzheimer's disease, Huntington's disease, Parkinson's disease and epilepsy; erythromelalgic or post-poliomyelitic pain, trigeminal or post-herpetic neuralgia.

In addition, the invention provides a process for the production of a substituted 1-aminobutan-3-ol derivative according to the invention as illustrated in the following description and examples.

General Production of the Compounds According to the Invention

Reactions described in the literature (R. C. Larock, Comprehensive Organic Transformations, $2^{nd}$ Edition, Wiley, New York 1999 and literature cited therein) as well as experimental procedures known in-house were used for the syntheses. Substituted 1-aminobutan-3-ol derivatives of the general formula I can be prepared by a process which is characterised in that a β-aminoketone (hereinafter also termed Mannich bases) of the formula Ia, in which the radicals $R^1$ to $R^4$, $R^6$ and $R^7$ have one of the meanings described above for formula I, this reaction being particularly preferred for compounds in which $R^6 \neq H$,

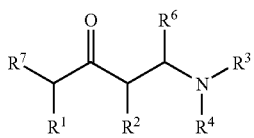
Ia is reacted with an organometallic compound of the formula III $$R^5-Z \quad III$$

in which Z denotes MgCl, MgBr, MgI or Li and $R^5$ has one of the meanings given above for formula I, to form a compound of the formula I.

The reaction of a β-aminoketone Ia with a Grignard compound of the formula III in which Z denotes MgCl, MgBr or MgI, or with an organolithium compound of the formula III, may be carried out in an aliphatic ether, for example diethyl ether and/or tetrahydrofuran, at temperatures between −70° C. and +60° C. Organolithium compounds of the formula III in which Z denotes Cl, Br or I can be obtained by halogen-lithium exchange by reaction with for example an n-butyllithium/hexane solution.

β-aminoketones of the general formula Ia can be prepared by processes known in the literature (Houben-Weyl—Methoden der Organischen Chemie, E21b, 1995, pp. 1925–1929; M. Tramontini, L. Angiolini, Mannich Bases, Chemistry and Uses, CRS Press, 1994 and literature cited therein). Preferably, β-aminoketones of the general formula Ia can be obtained by reacting enamines of the general formula IV, this reaction being particularly preferred for compounds in which $R^6 \neq H$,

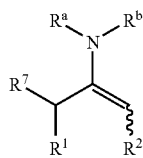
IV with an iminium salt of the general formula V,

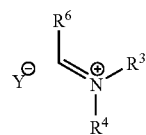
V wherein Y preferably denotes Cl⁻, AlCl₄⁻, Br⁻ or I⁻.

Compounds in which $R^6$ corresponds to H may be prepared in a similar way to the conventional Mannich reaction processes known in the literature via the Eschnmoser salt or BuLi.

The enamines of the general formula IV are obtained by processes known in the literature by reacting ketones of the general formula VI

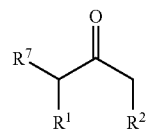
VI with secondary amines, preferably dimethylamine, pyrrolidine, piperidine or morpholine (Acta Chem. Scand. Vol. 38, 1984, pp. 49–53). The iminium salts of the general formula V are prepared by processes known in the literature by reacting aminals of the general formula VII

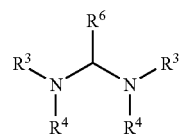
VII with acid chlorides, for example acetyl chloride or thionyl chloride (Houben-Weyl—Methoden der Organischen Chemie, E21b, 1995, pp. 1925–1929).

The iminium salts of the general formula V do not have to be isolated, but can be prepared in situ and reacted with enamines of the general formula IV to form Mannich bases of the general formula Ia (Angew. Chem. 106, 1994, pp. 2531–2533). On account of the enamine-imine tautomerism analogous to the keto-enol tautomerism, instead of the enamines of the general formula IV imines of the general formula VIII may also be used

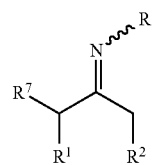
VIII

Alternatively, ketones of the general formula VI may also be reacted directly with iminium salts of the general formula V.

Mannich bases of the general formula Ia may however also be prepared directly by reacting enamines of the general formula IV with an aromatic or heteroaromatic aldehyde of the general formula IX

IX and a secondary amine of the general formula $HNR^3R^4$ (X), also in the form of the corresponding hydrochloride $HNR^3R^4 \cdot HCl$, preferably in the presence of triethylamine, chlorotrimethylsilane and sodium iodide (Synlett 1997, pp. 974–976).

The Mannich bases of the general formula Ia are obtained by the aforedescribed processes and, depending on the reaction conditions, preferably with the relative configuration of the general formula IIa,

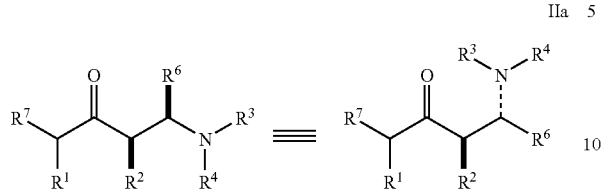

in which the amino group is arranged anti to $R^2$. These compounds of the general formula IIa can be obtained in diastereomer-pure form by crystallisation, also by crystallisation of their salts, for example the hydrochlorides, or by chromatographic separation.

The preparation of Mannich bases of the general formula Ia by 1,4-addition of secondary amines of the general formula X to enones of the general formula XI,

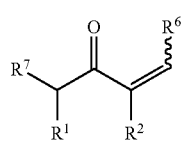

which are obtained from the aldol condensation of ketones of the general formula VI with aromatic or heteroaromatic aldehydes of the general formula IX, on the other hand proceeds less stereoselectively (U.S. Pat. No. 4,017,637). This procedure is accordingly suitable for the preparation of the other possible stereoisomers.

If chiral amines are used to prepare enamines of the general formula IV or imines of the general formula VIII, then enantiomer-enriched to enantiomer-pure Mannich bases of the general formula Ia may be obtained in the subsequent Mannich reaction (Houben-Weyl—Methoden der Organischen Chemie, E21b, 1995, pp. 1925–1929).

Enantiomer-pure Mannich bases of the formula Ia may also be obtained by an aminomethylation using enantiomer-pure ketones of the formula VI (if $R^6$ and $R^7$ are different) or may be prepared by racemate resolution via the crystallisation of diastereomeric salts using chiral acids, preferably tartaric acid, tartaric acid derivatives or mandelic acid (J. Gawronski, K. Gawronska, Tartaric and Malic Acids in Synthesis, Wiley, N.Y. 1999 and literature cited therein).

The diastereomeric Mannich bases formed in the aminomethylation reaction can be obtained in diastereomer-pure form either by column chromatography separation or by fractional crystallisation of their hydrochlorides from an organic solvent such as for example 2-butanone or acetone.

Ketones of the formula VI were either obtained commercially or were synthesised by processes known in the literature. Ketones of the formula VI where $R^7$ denotes $C_{1-6}$-alkyl, aryl, heteroaryl, alkylaryl or alkylheteroaryl can be obtained by processes described in the literature by α-addition of ketones of the formula XII

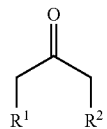

Various processes have been described for the regioselective α-addition via enol ethers, enolates or enoxydialkylboranes (for example I. Kuwajima et al., J. Am. Chem. Soc. 1982, 104, 1025; H. O. House, Modern Synthetic Reactions, $2^{nd}$ Edition, Benjamin, Menlo Park, Calif., 1972, J. K. Rasmussen, Synthesis 1977, 91, E. -I. Negishi et al., Tetrahedron Lett. 1979, 845). The use of α-metallated hydrazones of enolisable ketones as enolate equivalents via the reaction sequence carbonyl compound, hydrazone derivative, metallation, reaction with halides and subsequent cleavage by oxidative hydrolysis to form the α-substituted carbonyl compound has been described in detail by Enders et al. (D. Enders, W. Bettray, Pure Appl. Chem. 1996, 69, 569–580. Recent Advances in the Development of Highly Enantioselective Synthetic Methods and D. Enders in Asymmetric Synthesis Vol. 3, J. D. Morrison (Ed.), Academic Press, Orlando, 1984, 275–339, Alkylation of Chiral Hydrazones). Enantiomer-pure ketones of the formula VI may also be obtained by these processes by using chiral hydrazones (SAMP method). The metallation of hydrazones is carried out quantitatively with bases such as for example lithium diisopropylamide, wherein the subsequent reaction of the metallated hydrazones with halides to form the α-substituted hydrazones likewise proceeds with high yields. As an alternative to reacting metallated hydrazones, metalloenamines can also be reacted with halides (see for example I. Paterson et al., Tetrahedron 1990, 46, 4663).

Ketones of the general formula VI can also be prepared by oxidation of the corresponding alcohols of the general formula XIII, $R^1$, $R^2$ and $R^7$ having the same meanings as in the general formula I.

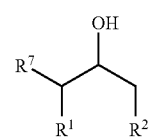

Compounds of the formula XIII can be prepared from the corresponding olefins of the formulae XIVa and XIVb, where $R^1$, $R^2$ and $R^7$ have the same meanings as in the general formula I, by hydroboration, preferably using 9-borobicyclo[3.3.0]nonane as reducing agent followed by oxidative working-up, preferably using hydrogen peroxide in an alkaline pH range (see e.g. H. C. Brown et al., J. Am. Chem. Soc. 1977, 99, 3427).

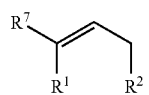

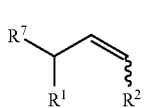

Hydroxyl derivatives of the formula XIII may also be obtained by cuprate-catalysed opening of the corresponding oxirane derivatives (epoxides) of the formula XV by nucleophilic agents, preferably Grignard compounds or organolithium compounds of the type $R^7$-Z (XVI) (see e.g. C. Huyn et al., Tetrahedron Lett. 1979, 1503; J. K. Whitesell et al., Chimia 1986, 40, 318), wherein Z has the same meaning as in formula III and $R^7$ is $C_{1-6}$-alkyl, aryl, heteroaryl, alkylaryl or alkylheteroaryl. The enantiomer-pure alcohols of XIII can also be obtained by enzymatic racemate resolution.

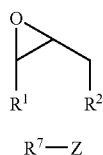

Alcohols of the formula XIII in which $R^7$ denotes a halogen can be converted, for example by reacting the oxirane derivatives of the formula XV with lithium halides in the presence of acids, into the corresponding alcohols of the formula XIII where $R^7$ is halogen (J. S. Bagwa et al., Tetrahedron Lett. 1991, 32, 3021). Compounds of the formula (X) in which $R^7$ is bromine can be obtained by reacting olefins of the formulae (XIVa, b) with N-bromosuccinimide in water (C. O. Guss, J. Am. Chem. Soc. 1955, 77, 2549).

Substituted 1-aminobutan-3-ol derivatives of the formula I in which $R^5$ represents a phenol group can be prepared from the methoxyaryl derivatives by selective ether cleavage, for example with diisobutylaluminium hydride in an aromatic hydrocarbon, for example toluene, at a temperature between 60° and 130° C. (Synthesis 1975, 617; DBP 2409990, 2409991 and Chem. Abstr. 84, 59862 (19974)).

Furthermore, 1-aminobutan-3-ol derivatives of the formula I in which $R^5$ represents a phenol group can be obtained from the corresponding benzyloxy-arylenes by reductive debenzylation. The debenzylation is preferably carried out in the presence of platinum or palladium on a carrier material such as activated charcoal absorbed as catalyst, in the presence of hydrogen in a solvent such as acetic acid or a $C_{1-4}$-alkyl alcohol at pressures of 1 to 100 bar and temperatures of 20°–100° C.

Salt Formation

The compounds of the formula I can be converted into their salts in a manner known per se with physiologically acceptable acids, for example hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydrol$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The salt formation is preferably carried out in a solvent, for example diethyl ether, diisopropyl ether, alkyl esters of acetic acid, acetone and/or 2-butanone or also water. For the production of the hydrochlorides, trimethylchlorosilane in aqueous solution is moreover suitable.

Synthesis of Compounds in which $R^6$ is other than Hydrogen:

These compounds have been prepared by processes such as are described in the literature, for example Risch et al., Houben-Weyl—Methoden der Organischen Chemie, E21b (1995) 1925–1929; Angew. Chem. 106 (1994) 2531–2533; Synlett (1997) 974–976.

The invention is described in more detail hereinafter by examples, without however being restricted to the latter.

EXAMPLES

The following examples illustrate compounds according to the invention as well as their preparation and effectiveness investigations carried out using these compounds. The following details apply in general:

The chemicals and solvents used were commercially obtained from customary suppliers (Acros, Avocado, Aldrich, Fluka, Lancaster, Maybridge, Merck, Sigma, TCI etc. or were synthesised).

The analysis was carried out by ESI mass spectrometry and/or HPLC and/or NMR spectroscopy.

The Mannich base (400 μl, 0.5 mole/l) dissolved in THF was added to a previously thoroughly heated reaction vessel cooled under an inert gas to −10° C. Two equivalents of the prepared Grignard or organolithium reagent (0.5 mole/l in THF or diethyl ether, 800 μl) were then added while stirring. The reaction mixture was stirred at room temperature. After 3 hours the reaction mixture was re-cooled to −10° C. and hydrolysed with ammonium chloride solution. The reaction mixture was extracted twice with ethyl acetate and concentrated by evaporation at 40° C. in vacuo.

An ESI-MS was recorded to characterise the chlorinated compounds. An NMR spectrum was recorded to characterise the remaining compounds.

Example of the Synthesis of 1-(3-chlorophenyl)-2-dimethylaminomethyl-6-(4-methoxyphenyl)-cyclohexanol hydrochloride

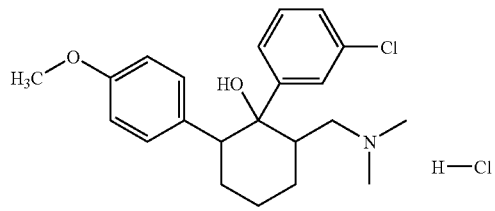

1$^{st}$ Stage: 2-(4-methoxyphenyl)-cyclohexanol

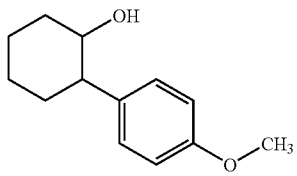

The reaction was carried out under nitrogen as protective gas. 19.4 g (0.8 mole) of magnesium turnings were stirred in 50 ml of dry tetrahydrofuran. 100 ml (150 g, 0.8 mole) of 1-bromo-4-methoxybenzene dissolved in 300 ml of absolute tetrahydrofuran were added dropwise so that the reaction mixture boiled. The reaction mixture was then heated for an hour under reflux before being cooled to 10° C. 14.9 g of copper iodide were next added in portions at this temperature. The reaction solution was stirred for 1 hour. 81 ml (78.6 g, 0.8 mole) of 7-oxa-bicyclo[4.1.0]heptane dissolved in 160 ml of dry tetrahydrofuran were then added dropwise at such a rate that the internal temperature of the strongly exothermic reaction did not exceed 25° C. (cooling with acetone/dry ice). After completion of the addition the reaction mixture was stirred overnight at room temperature.

The reaction mixture was hydrolysed, while cooling in an ice bath, first of all by adding 90 ml of water, following which a mixture consisting of 17 g of ammonium chloride, 50 ml of conc. hydrochloric acid and 350 ml of water was added dropwise. After separating the phases the aqueous phase was extracted three times with 250 ml of diethyl ether. The combined organic phases were washed twice with in each case 150 ml of saturated sodium hydrogen carbonate solution. After filtration through 200 g of silica gel the product was dried over sodium sulfate. After removal of the solvent by distillation, 150 g (89% of theory) of pale yellow, waxy crystals were obtained, which were used without further purification in the next stage.

2$^{nd}$ Stage: 2-(4-methoxyphenyl)-cyclohexanone

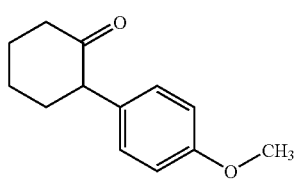

146 g (0.71 mole) of 2-(4-methoxyphenyl)-cyclohexanol from the 1$^{st}$ stage were dissolved in 600 ml of diethyl ether. A solution consisting of 69.9 g (0.23 mole) of sodium dichromate (as dihydrate), 355 ml of water and 53.2 ml of conc. sulfuric acid was added dropwise while stirring vigorously and cooling in an ice bath so that the internal temperature did not exceed 10° C. After completion of the addition the reaction mixture was stirred overnight at room temperature. After separating the phases the aqueous phase was then extracted twice with 200 ml of diethyl ether. The combined organic phases were washed twice with 200 ml of saturated sodium hydrogen carbonate solution and dried over sodium sulfate. After removing the solvent by distillation the remaining oil was distilled and the fraction passing over at 128–134° C./0.05 bar was collected. After crystallisation from n-hexane 130 g of colourless crystals with a melting point of 90° C. were obtained (90% of theory).

3$^{rd}$ Stage: 2-dimethylaminomethyl-6-(4-methoxyphenyl)-cyclohexanone

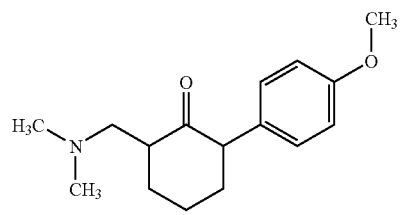

200 g (0.98 mole) of 2-(4-methoxyphenyl)-cyclohexanone from stage 2 and 91 g (1 mole) of dimethylammonium ethylene chloride were stirred in 1000 ml of dry acetonitrile at room temperature. After addition of 1 ml of acetyl chloride the reaction mixture was stirred for a further 3 hours at room temperature, a colourless, clear solution being formed. 2000 ml of dry ether were then added dropwise to the reaction mixture and the hydrochloride crystallised out. 160 g (56% of theory) of colourless crystals were obtained. The base was freed from the hydrochloride with dichloromethane/sodium hydroxide and, after drying the solution, the dichloromethane was removed by distillation.

This is a generally valid example that illustrates the use of the processes known in the literature for producing compounds where $R^6$=H.

4$^{th}$ Stage: 1-(3-chlorophenyl)-2-dimethylaminomethyl-6-(4-methoxyphenyl)-cyclohexanol hydrochloride The reaction was carried out under nitrogen as protective gas. 18.3 g (0.75 mole) of magnesium turnings were stirred in 150 ml of dry tetrahydrofuran. 88 ml (144 g, 0.75 mole) of 1-bromo-3-chlorobenzene dissolved in 500 ml of absolute tetrahydrofuran were added dropwise so that the reaction mixture boiled. The reaction mixture was then stirred under reflux for 1 hour before being cooled to 10° C. Following this 131 g (0.5 mole) of 2-dimethylaminomethyl-6-(4-methoxyphenyl)-cyclohexanone from stage 3, dissolved in 400 ml of dry tetrahydrofuran, were added dropwise at such a rate that the internal temperature did not exceed 20° C. After completion of the addition the reaction mixture was stirred overnight at room temperature.

The reaction mixture was hydrolyzed by adding 1000 ml of 20% ammonium chloride solution while cooling in an ice bath. After separating the phases the aqueous phase was extracted three times with 250 ml of diethyl ether. The combined organic phases were washed twice with in each case 100 ml of saturated sodium hydrogen carbonate solution. After removing the solvent by distillation, 166 g (93% of theory) of a pale yellow oil were obtained as crude product.

The resulting crude product was added to an 8×60 cm column packed with silica gel and eluted with ethyl acetate/methanol in a ratio of 1:1. 91.7 g of pure base were obtained (52% of theory). The base was taken up in 920 ml of 2-butanone, and 31.1 ml of trimethylchlorosilane and 4.4 ml of water were added. 58.7 g (31.4% of theory) of hydrochloride having a melting point of 243° C. crystallised out overnight at 4–5° C.

| | Name |
|---|---|
| Example 1 | 2-benzyl-1-(2,4-dichlorobenzyl)-6-dimethyl-aminomethylcyclohexanol |
| Example 2 | 2-benzyl-1-(3-chlorobenzyl)-6-dimethylamino-methylcyclohexanol |
| Example 3 | 2-benzyl-6-dimethylaminomethyl-1-(2,5-dimethylbenzyl)-cyclohexanol |
| Example 4 | 2-benzyl-1-(2-chloro-6-fluorobenzyl)-6-dimethylaminomethylcyclohexanol |
| Example 5 | 2-benzyl-1-(4-chlorobenzyl)-6-dimethylamino-methylcyclohexanol |
| Example 6 | 2-benzyl-6-dimethylaminomethyl-1-(3-trifluoro-methylphenyl)-cyclohexanol |
| Example 7 | 2-benzyl-6-dimethylaminomethyl-1-(2-methyl-benzyl)-cyclohexanol |
| Example 8 | 2-benzyl-6-dimethylaminomethyl-1-(2-methoxy-phenyl)-cyclohexanol |
| Example 9 | 2-benzyl-1-(4-chloro-3-trifluoromethylphenyl)-6-dimethylaminomethylcyclohexanol |
| Example 10 | 2-benzyl-1-(2-chlorobenzyl)-6-dimethylamino-methylcyclohexanol |
| Example 11 | 2-benzyl-1-(3,5-dichlorophenyl)-6-dimethyl-aminomethylcyclohexanol |
| Example 12 | 2-benzyl-1-(3-chlorophenyl)-6-dimethylamino-methylcyclohexanol |
| Example 13 | 2-benzyl-6-dimethylaminomethyl-1-(3-fluoro-phenyl)-cyclohexanol |
| Example 14 | 2-benzyl-6-dimethylaminomethyl-1-(5-fluoro-2-methoxyphenyl)-cyclohexanol |
| Example 15 | 2-benzyl-1-cyclohexylmethyl-6-dimethyl-aminomethylcyclohexanol |
| Example 16 | 2-benzyl-6-dimethylaminomethyl-1-(4-methoxy-phenyl)-cyclohexanol |
| Example 17 | 2-benzyl-6-dimethylaminomethyl-1-p-tolyl-cyclohexanol |
| Example 18 | 2-benzyl-6-dimethylaminomethyl-1-(3-phenyl-propyl)-cyclohexanol |
| Example 19 | 2-benzyl-6-dimethylaminomethyl-1-(3-methoxy-phenyl)-cyclohexanol |
| Example 20 | 2-benzyl-6-dimethylaminomethyl-1-thiophen-2-yl-cyclohexanol |
| Example 21 | 2-benzyl-6-dimethylaminomethyl-1-phenylethynyl-cyclohexanol |
| Example 22 | 2-benzyl-6-dimethylaminomethyl-1-(4-fluoro-phenyl)-cyclohexanol |
| Example 23 | 2-benzyl-6-dimethylaminomethylbicyclohexyl-1-ol |
| Example 24 | 2-benzyl-6-dimethylaminomethyl-1-m-tolyl-cyclohexanol |
| Example 25 | 2-benzyl-1-(4-tert.-butylphenyl)-6-dimethyl-aminomethylcyclohexanol |
| Example 26 | 2-benzyl-6-dimethylaminomethyl-1-vinyl-cyclohexanol |
| Example 27 | 2-benzyl-6-dimethylaminomethyl-1-o-tolyl-cyclohexanol |
| Example 28 | 2-benzyl-6-dimethylaminomethyl-1-(4-fluoro-3-methylphenyl)-cyclohexanol |
| Example 29 | 1,2-dibenzyl-6-dimethylaminomethylcyclohexanol |
| Example 30 | 2-benzyl-1-(4-chlorophenyl)-6-dimethylamino-methylcyclohexanol |
| Example 31 | 2-benzyl-6-dimethylaminomethyl-1-phenyl-cyclohexanol |
| Example 32 | 2-dimethylaminomethyl-1-(2,5-dimethylphenyl)-6-(3-methoxyphenyl)-cyclohexanol |
| Example 33 | 1-cyclohexylmethyl-2-dimethylaminomethyl-6-(3-methoxyphenyl)-cyclohexanol |
| Example 34 | 1-(2,4-dichlorobenzyl)-2-dimethylaminomethyl-6-(3-methoxyphenyl)-cyclohexanol |
| Example 35 | 2-dimethylaminomethyl-6-(3-methoxyphenyl)-1-phenylethynylcyclohexanol |
| Example 36 | 2-dimethylaminomethyl-6-(3-methoxyphenyl)-1-o-tolylcyclohexanol |
| Example 37 | 1-(4-chlorophenyl)-2-dimethylaminomethyl-6-(3-methoxyphenyl)-cyclohexanol |
| Example 38 | 2-dimethylaminomethyl-1-(3-fluorophenyl)-6-(3-methoxyphenyl)-cyclohexanol |
| Example 39 | 2-dimethylaminomethyl-1-(3-fluoro-4-methoxy-phenyl)-6-(3-methoxyphenyl)-cyclohexanol |
| Example 40 | 1-(3-chlorobenzyl)-2-dimethylaminomethyl-6-(3-methoxyphenyl)-cyclohexanol |
| Example 41 | 2-dimethylaminomethyl-1-(3-methoxybenzyl)-6-(3-methoxyphenyl)-cyclohexanol |
| Example 42 | 1-(4-chloro-3-trifluoromethylphenyl)-2-dimethylaminomethyl-6-(3-methoxyphenyl)-cyclohexanol |
| Example 43 | 1-(3,5-dichlorobenzyl)-2-dimethylaminomethyl-6-(3-methoxyphenyl)-cyclohexanol |
| Example 44 | 2-dimethylaminomethyl-6-(3-methoxyphenyl)-1-phenylethynylcyclohexanol |
| Example 45 | 1-(4-chlorophenyl)-2-dimethylaminomethyl-6-(3-methoxyphenyl)-cyclohexanol |
| Example 46 | 2-dimethylaminomethyl-6-(3-methoxyphenyl)-1-o-tolylcyclohexanol |
| Example 47 | 1-(3-chlorobenzyl)-2-dimethylaminomethyl-6-methylcyclohexanol |
| Example 48 | 2-dimethylaminomethyl-1-(2,5-dimethylbenzyl)-6-methylcyclohexanol |
| Example 49 | 1-(2-chloro-6-fluorobenzyl)-2-dimethylamino-methyl-6-methylcyclohexanol |
| Example 50 | 1-(4-chlorobenzyl)-2-dimethylaminomethyl-6-methylcyclohexanol |
| Example 51 | 2-dimethylaminomethyl-6-methyl-1-(3-methyl-benzyl)-cyclohexanol |
| Example 52 | 2-dimethylaminomethyl-6-methyl-1-(3-trifluoromethyl-phenyl)-cyclohexanol |
| Example 53 | 1-(2-chloro-3-fluorophenyl)-2-dimethylamino-methyl-6-methylcyclohexanol |
| Example 54 | 2-dimethylaminomethyl-6-methyl-1-(2-methyl-benzyl)-cyclohexanol |
| Example 55 | 2-dimethylaminomethyl-1-(2-methoxyphenyl)-6-methylcyclohexanol |
| Example 56 | 2-dimethylaminomethyl-1-(3-fluorobenzyl)-6-methylcyclohexanol |
| Example 57 | 2-dimethylaminomethyl-1-(4-fluorobenzyl)-6-methylcyclohexanol |
| Example 58 | 1-(2-chlorobenzyl)-2-dimethylaminomethyl-6-methylcyclohexanol |
| Example 59 | 1-(3,5-dichlorophenyl)-2-dimethylaminomethyl-6-methylcyclohexanol |
| Example 60 | 1-(3-chlorophenyl)-2-dimethylaminomethyl-6-methylcyclohexanol |
| Example 61 | 2-dimethylaminomethyl-1-(3-fluorophenyl)-6-methylcyclohexanol |
| Example 62 | 2-dimethylaminomethyl-1-(3-fluoro-4-methoxy-phenyl)-6-methylcyclohexanol |
| Example 63 | 2-dimethylaminomethyl-1-(4-methoxyphenyl)-6-methylcyclohexanol |
| Example 64 | 2-dimethylaminomethyl-6-methyl-1-p-tolyl-cyclohexanol |
| Example 65 | 2-dimethylaminomethyl-6-methyl-1-(3-phenyl-propyl)-cyclohexanol |
| Example 66 | 2-dimethylaminomethyl-1-(3-methoxyphenyl)-6-methylcyclohexanol |
| Example 67 | 2-dimethylaminomethyl-6-methyl-1-thiophen-2-yl-cyclohexanol |
| Example 68 | 2-dimethylaminomethyl-6-methyl-1-phenylethynyl-cyclohexanol |
| Example 69 | 2-dimethylaminomethyl-6-methyl-1-phenethyl-cyclohexanol |
| Example 70 | 2-dimethylaminomethyl-1-(4-fluorophenyl)-6-methylcyclohexanol |
| Example 71 | 1-(3-chlorobenzyl)-2-dimethylaminomethyl-6-(3-methoxyphenyl)-cyclohexanol |
| Example 72 | 2-dimethylaminomethyl-1-(4-fluoro-2-methoxy-phenyl)-6-(3-methoxyphenyl)-cyclohexanol |
| Example 73 | 2-dimethylaminomethyl-1-(2-methoxyphenyl)-6-(3-methoxyphenyl)-cyclohexanol |
| Example 74 | 2-dimethylaminomethyl-1-(4-fluorobenzyl)-6-(3-methoxyphenyl)-cyclohexanol |
| Example 75 | 1-(3-chlorophenyl)-2-dimethylaminomethyl-6-(3-methoxyphenyl)-cyclohexanol |
| Example 76 | 2-dimethylaminomethyl-6-(3-methoxyphenyl)-1-p-tolylcyclohexanol |
| Example 77 | 2-dimethylaminomethyl-6-(3-methoxyphenyl)-1-(3-phenylpropyl)-cyclohexanol |

| | Name |
|---|---|
| Example 78 | 2-dimethylaminomethyl-1,6-bis-(3-methoxy-phenyl)-cyclohexanol |
| Example 79 | 2-dimethylaminomethyl-6-(3-methoxyphenyl)-1-thiophen-2-yl-cyclohexanol |
| Example 80 | 2-dimethylaminomethyl-6-(3-methoxyphenyl)-1-phenethyl-cyclohexanol |
| Example 81 | 3-[3-dimethylaminomethyl-2-(4-fluorophenyl)-2-hydroxycyclohexyl]-phenol |
| Example 82 | 3-(3-dimethylaminomethyl-2-hydroxy-2-phenyl-cyclohexyl)-phenol |
| Example 83 | 3-[2-(4-tert.-butylphenyl)-3-dimethylamino-methyl-2-hydroxycyclohexyl]phenol |
| Example 84 | 3-(3-dimethylaminomethyl-2-hydroxy-2-vinyl-cyclohexyl)-phenol |
| Example 85 | 1-(4-chlorophenyl)-2-dimethylaminomethyl-6-(3-methoxyphenyl)-cyclohexanol |
| Example 86 | 3-dimethylaminomethyl-2-(3-methoxyphenyl)-bicyclohexyl-2-ol |
| Example 87 | 2-benzyl-6-dimethylaminomethyl-1-(4-trifluoro-methylphenyl)-cyclohexanol |
| Example 88 | 3-(2-benzyl-6-dimethylaminomethyl-1-hydroxy-cyclohexyl)-phenol |
| Example 89 | 3-(2-tert.-butyl-6-dimethylaminomethyl-1-hydroxycyclohexyl)-phenol |

Pharmacological Investigations

Gabapentin is used in the binding assay in order to check the binding and affinities of the selected compounds. The affinity of the compounds according to the invention is measured via the displacement of gabapentin from its binding site. If the selected compounds can displace gabapentin from its binding site, then it may be expected that they will exhibit pharmacological properties comparable to those of gabapentin, for example as an agent to control pain or epilepsy. The compounds according to the invention exhibit a good inhibition/displacement of gabapentin in this assay. The investigated compounds furthermore exhibit in this biochemical assay an affinity for the hitherto unknown gabapentin binding site.

| Example | % Inhibition Gabapentin, 10 μmole |
|---|---|
| 82 | 55 |
| 81 | 48 |
| 76 | 53 |
| 75 | 54 |
| 45 | 58 |

Analgesia Investigation in the Writhing Test in Mice

The analgesic effect was investigated using the phenylquinone-induced writhing test in mice (as modified by I. C. Hendershot and J. Forsaith, J. Pharmacol. Exp. Ther. 1959, 237–240). Male NMRI mice weighing 25–30 g were used for this purpose. Groups of 10 animals per substance dose were given intraperitoneally 10 minutes after intravenous administration of the test substances, 0.3 ml/mouse of a 0.02% aqueous solution of phenylquinone (phenylbenzoquinone, from Sigma, Deisenhofen; solution prepared by addition of 5% of ethanol and storage in a water at 45° C.). The animals were placed individually in observation cages. The number of pain-induced stretching movements (so-called writhing reactions=contortion of the body accompanied by stretching of the rear extremities) 5–20 minutes after administration of the phenylquinone were counted using a push-button counter. Animals that had received only physiological saline solution served as controls. The number of reacting anmials was determined for some of the examples:

| Example | Reacting Animals/Control Animals (Writhing) |
|---|---|
| 85 | 10/10 (46.4 mg/kg; iv) |
| 86 | 3/10 (21.5 mg/kg; po) |
| 87 | 2/10 (10 mg/kg; iv) |
| 88 | 2/10 (10 mg/kg; iv) |
| 89 | 3/10 (10 mg/kg; iv) |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A substituted 1-aminobutan-3-ol compound corresponding to the formula I

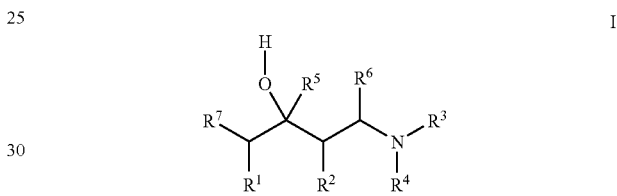

wherein $R^1$ and $R^2$ together form a $(CH_2)_{2-9}$ ring that may optionally be substituted with $C_{1-8}$-alkyl that is branched or unbranched, saturated or unsaturated, unsubstituted or singly or multiply substituted; or aryl that is unsubstituted or singly or multiply substituted, $R^3$ and $R^4$ are each independently selected from the group consisting of $C_{1-6}$-alkyl that is branched or unbranched, saturated or unsaturated, unsubstituted or singly or multiply substituted; $C_{3-6}$-cycloalkyl that is saturated or unsaturated, unsubstituted or singly or multiply substituted; phenyl, benzyl or phenethyl that is unsubstituted or singly or multiply substituted, or $R^3$ and $R^4$ together form a ring and denote $CH_2CH_2OCH_2CH_2$, $CH_2CH_2NR^{22}CH_2CH_2$ or $(CH_2)_{3-6}$ where $R^{22}$ is selected from the group consisting of H; $C_{1-10}$-alkyl or $C_{3-10}$-cycloalkyl, in each case saturated or unsaturated, branched or unbranched, singly or multiply substituted or unsubstituted; aryl or heteroaryl, in each case singly or multiply substituted or unsubstituted; or aryl, $C_{3-10}$-cycloalkyl or heteroaryl, in each case singly or multiply substituted or unsubstituted, and that is bound via a saturated or unsaturated $C_{1-3}$-alkyl group;

$R^5$ is selected from the group consisting of $C_{1-10}$-alkyl that is saturated or unsaturated, branched or unbranched, singly or multiply substituted or unsubstituted; saturated or unsaturated $C_{3-9}$-cycloalkyl; aryl, heteroaryl, aryl bound via saturated or unsaturated $C_{1-3}$-alkyl, $C_{3-10}$-cycloalkyl bound via saturated or unsaturated $C_{1-3}$-alkyl or heteroaryl bound via saturated or unsaturated $C_{1-3}$-alkyl, wherein the aryl, heteroaryl or cycloalkyl groups may each independently be unsubstituted or singly or multiply substituted with radicals selected independently of one another from the group consisting of F, Cl, Br, I, $OR^{18}$, $SR^{18}$, $SO_2R^{18}$, $SO_2OR^{18}$, CN, $COOR^{18}$, $NR^{19}R^{20}$; $C_{1-10}$-alkyl that is saturated or unsaturated, branched or unbranched, singly or multiply substituted or unsubstituted; $C_{3-9}$-cycloalkyl that is saturated or unsaturated, unsubstituted or singly or multiply substituted; aryl or heteroaryl, in each case unsubstituted or singly or multiply substituted; or aryl bound via saturated or unsaturated $C_{1-3}$-alkyl, $C_{3-9}$-cycloalkyl or heteroaryl, in each case unsubstituted or singly or multiply substituted;

where $R^{18}$ is selected from the group consisting of H; $C_{1-10}$-alkyl that is saturated or unsaturated, branched or unbranched, unsubstituted or singly or multiply substituted; $C_{3-9}$-cycloalkyl that is saturated or unsaturated, unsubstituted or singly or multiply substituted; aryl or heteroaryl that is unsubstituted or singly or multiply substituted; or aryl bound via saturated or unsaturated $C_{1-3}$-alkyl, $C_{3-9}$-cycloalkyl or heteroaryl, in each case unsubstituted or singly or multiply substituted;

$R^{19}$ and $R^{20}$ are independently selected from the group consisting of H; $C_{1-10}$-alkyl that is saturated or unsaturated, branched or unbranched, unsubstituted or singly or multiply substituted; $C_{3-9}$-cycloalkyl that is saturated or unsaturated, unsubstituted or singly or multiply substituted; aryl or heteroaryl in each case unsubstituted or singly or multiply substituted; or aryl bound via saturated or unsaturated $C_{1-3}$-alkyl, $C_{3-9}$-cycloalkyl or heteroaryl, in each case unsubstituted or singly or multiply substituted; or R19 and $R^{20}$ together form $CH_2CH_2OCH_2CH_2$, $CH_2CH_2NR^{21}CH_2CH_2$ or $(CH_2)_{3-6}$, where $R^{21}$ is selected from the group consisting of H, $C_{1-10}$-alkyl that is saturated or unsaturated, branched or unbranched, unsubstituted or singly or multiply substituted;

$R^6$ is selected from the group consisting of H; aryl or heteroaryl in each case unsubstituted or singly or multiply substituted; and $R^7$ is selected from the group consisting of halogen, $CF_3$; $C_{1-6}$-alkyl that is branched or unbranched, saturated or unsaturated, unsubstituted or singly or multiply substituted; $C_{3-9}$-cycloalkyl that is saturated or unsaturated, unsubstituted or singly or multiply substituted; aryl, heteroaryl that is in each case unsubstituted or singly or multiply substituted; aryl bound via saturated or unsaturated $C_{1-3}$-alkyl, $C_{3-9}$-cycloalkyl or heteroaryl, in each case unsubstituted or singly or multiply substituted optionally in the form of a racemate, a pure stereoisomer, an enantiomer or diastereomer, or a mixture of stereoisomers, of enantiomers or diastereomers, in an arbi-'trary mixture ratio; or a free acid or a free base or a physiologically acceptable salt, or a solvate or hydrate.

2. A compound according to claim 1, wherein $R^6$ is H or heteroaryl or a radical corresponding to formula II.

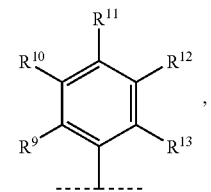

wherein
$R^9$ to $R^{13}$ are each independently selected from the group consisting of H, F, Cl, Br, I, $CF_3$, OH, $OR^{14}$, $OCF_3$, $SR^{14}$, $SO_2CH_3$, $SO_2CF_3$; $C_{1-6}$-alkyl that is branched or unbranched, saturated or unsaturated, unsubstituted or singly or multiply substituted; phenyl that is unsubstituted or singly or multiply substituted; CN, $COOR^{14}$, $NO_2$, or wherein
$R^9$ and $R^{10}$ or $R^{10}$ and $R^{11}$ together form an $OCH_2O$ or $OCH_2CH_2O$ ring, and $R^{14}$ is selected from the group consisting of $C_{1-6}$-alkyl that is branched or unbranched, saturated or unsaturated, unsubstituted or singly or multiply substituted; phenyl, benzyl, phenethyl or thiophenyl, in each case unsubstituted or singly or multiply substituted.

3. A compound according to claim 1, wherein $R^1$ and $R^2$ together form a $(CH_2)_{2-5}$ ring that may optionally be substituted by $C_{1-6}$-alkyl that is branched or unbranched, saturated or unsaturated, unsubstituted or singly or multiply substituted; or phenyl that is unsubstituted or singly or multiply substituted.

4. A compound according to claim 3, wherein $R^1$ and $R^2$ together form a $(CH_2)_{2-5}$ ring that is substituted by unsubstituted phenyl.

5. A compound according to claim 1, wherein
$R^3$ and $R^4$ are each independently selected from $C_{1-6}$-alkyl that is branched or unbranched, saturated or unsaturated, unsubstituted or singly or multiply substituted; or
$R^3$ and $R^4$ together form a ring and denote $(CH_2)_{3-6}$ or $CH_2CH_2NR^{22}CH_2CH_2$, where $R^{22}$ is H or saturated and unsubstituted $C_{1-6}$-alkyl that is branched or unbranched.

6. A compound according to claim 5, wherein $R^3$ and $R^4$ both denote $CH_3$.

7. A compound according to claim 5, wherein $R^3$ and $R^4$ together denote $(CH_2)_{4-5}$ or $CH_2CH_2NR^{22}CH_2CH_2$, where $R^{22}$ is H or $CH_3$.

8. A compound according to claim 1, wherein $R^5$ is selected from the group consisting of $C_{1-6}$-alkyl that is saturated or unsaturated, branched or unbranched, singly or multiply substituted or unsubstituted; $C_{5-6}$-cycloalkyl; phenyl; thiophenyl; furyl; benzofuranyl; benzothiophenyl; pyrrolyl; pyridinyl; pyrimidinyl; quinolinyl; isoquinolinyl; quinazolinyl; phenyl bonded via saturated or unsaturated $C_{1-3}$-alkyl; $C_{5-6}$-cycloalkyl bonded via saturated or unsaturated $C_{1-3}$-alkyl; or thiophenyl, furyl, benzofuranyl, benzothiophenyl, pyrrolyl, pyridinyl, pyrimidinyl, quinolinyl, isoquinolinyl, quinazolinyl bonded via saturated or unsaturated $C_{1-3}$-alkyl;

wherein any aryl, heteroaryl and cycloalkyl groups may in each case independently of one another be unsubstituted or singly or multiply substituted.

9. A compound according to claim 8, wherein $R^5$ is
   phenyl or thiophenyl that is unsubstituted or singly or multiply substituted, with F, Cl, Br, I, OH, O—$C_{1-4}$-alkyl, $C_{1-6}$-alkyl, $NH_2$ and/or SH; or
   phenyl bonded via saturated or unsaturated $C_{1-3}$-alkyl and that is unsubstituted or singly or multiply substituted with F, Cl, Br, I, OH, O—$C_{1-4}$-alkyl, $C_{1-6}$-alkyl, $NH_2$ and/or SH.

10. A compound according to claim 9, wherein $R^5$ is phenyl that is unsubstituted or singly or multiply substituted, with F, Cl, Br, I, OH, $OCH_3$, $OC_2H_5$, $OC_3H_7$, SH, $CH_3$, $C_2H_5$, $C_3H_7$ and/or $C_4H_9$.

11. A compound according to claim 1, wherein $R^7$ is selected from the group consisting of $C_{1-6}$-alkyl that is branched or unbranched, saturated or unsaturated, unsubstituted or singly or multiply substituted; $C_{5-7}$-cycloalkyl that is saturated or unsaturated, unsubstituted or singly or multiply substituted; phenyl that is unsubstituted or singly or multiply substituted; and phenyl that is bonded via saturated or unsaturated $C_{1-3}$-alkyl, and is unsubstituted or singly or multiply substituted.

12. A compound according to claim 11, wherein $R^7$ is cyclohexyl.

13. A compound according to claim 11, wherein $R^7$ is phenyl that is unsubstituted or singly or multiply substituted; or phenyl that is bonded via saturated or unsaturated $C_{1-3}$-alkyl and is unsubstituted or singly or multiply substituted.

14. A compound according to claim 1, wherein $R^5$ or $R^7$ is an aryl, $C_{3-9}$-cycloalkyl or heteroaryl group bound via saturated or unsaturated $C_{1-3}$-alkyl, and the $C_{1-3}$-alkyl via which the aryl, cycloalkyl or heteroaryl group is bound is selected from the group consisting of —$CH_2$—, —$C_2H_4$—, —$C_3H_6$—, —C≡C—, —CH═CH—, —CH═CH—$CH_2$—, —$CH_2$—CH═CH—, —C≡C—$CH_2$— and —$CH_2$—C≡C—.

15. A compound according to claim 14, wherein the $C_{1-3}$-alkyl is —$CH_2$—, —$C_2H_4$— or —C≡C—.

16. A compound according to claim 1, selected from the group consisting of:
   2-benzyl-1-(2,4-dichlorobenzyl)-6-dimethylaminomethylcyclohexanol
   2-benzyl-1-(3-chlorobenzyl)-6-dimethylaminomethylcyclohexanol
   2-benzyl-6-dimethylaminomethyl-1-(2,5-dimethylbenzyl)-cyclohexanol
   2-benzyl-1-(2-chloro-6-fluorobenzyl)-6-dimethylaminomethylcyclohexanol
   2-benzyl-1-(4-chlorobenzyl)-6-dimethylaminomethylcyclohexanol
   2-benzyl-6-dimethylaminomethyl-1-(3-trifluoromethylphenyl)-cyclohexanol
   2-benzyl-6-dimethylaminomethyl-1-(2-methylbenzyl)-cyclohexanol
   2-benzyl-6-dimethylaminomethyl-1-(2-methoxyphenyl)-cyclohexanol
   2-benzyl-1-(4-chloro-3-trifluoromethylphenyl)-6-dimethylaminomethylcyclohexanol
   2-benzyl-1-(2-chlorobenzyl)-6-dimethylaminomethylcyclohexanol
   2-benzyl-1-(3,5-dichlorophenyl)-6-dimethylaminomethylcyclohexanol
   2-benzyl-1-(3-chlorophenyl)-6-dimethylaminomethylcyclohexanol
   2-benzyl-6-dimethylaminomethyl-1-(3-fluorophenyl)-cyclohexanol
   2-benzyl-6-dimethylaminomethyl-1-(5-fluoro-2-methoxyphenyl)-cyclohexanol
   2-benzyl-1-cyclohexylmethyl-6-dimethylaminomethylcyclohexanol
   2-benzyl-6-dimethylaminomethyl-1-(4-methoxyphenyl)-cyclohexanol
   2-benzyl-6-dimethylaminomethyl-1-p-tolylcyclohexanol
   2-benzyl-6-dimethylaminomethyl-1-(3-phenylpropyl)-cyclohexanol
   2-benzyl-6-dimethylaminomethyl-1-(3-methoxyphenyl)-cyclohexanol
   2-benzyl-6-dimethylaminomethyl-1-thiophen-2-yl-cyclohexanol
   2-benzyl-6-dimethylaminomethyl-1-phenylethynylcyclohexanol
   2-benzyl-6-dimethylaminomethyl-1-(4-fluorophenyl)-cyclohexanol
   2-benzyl-6-dimethylaminomethylbicyclohexyl-1-ol
   2-benzyl-6-dimethylaminomethyl-1-m-tolylcyclohexanol
   2-benzyl-1-(4-tert.-butylphenyl)-6-dimethylaminomethylcyclohexanol
   2-benzyl-6-dimethylaminomethyl-1-vinylcyclohexanol
   2-benzyl-6-dimethylaminomethyl-1-o-tolylcyclohexanol
   2-benzyl-6-dimethylaminomethyl-1-(4-fluoro-3-methylphenyl)-cyclohexanol
   1,2-dibenzyl-6-dimethylaminomethylcyclohexanol
   2-benzyl-1-(4-chlorophenyl)-6-dimethylaminomethylcyclohexanol
   2-benzyl-6-dimethylaminomethyl-1-phenylcyclohexanol
   2-dimethylaminomethyl-1-(2,5-dimethylphenyl)-6-(3-methoxyphenyl)-cyclohexanol
   1-cyclohexylmethyl-2-dimethylaminomethyl-6-(3-methoxyphenyl)-cyclohexanol
   1-(2,4-dichlorobenzyl)-2-dimethylaminomethyl-6-(3-methoxyphenyl)-cyclohexanol
   2-dimethylaminomethyl-6-(3-methoxyphenyl)-1-phenylethynylcyclohexanol
   2-dimethylaminomethyl-6-(3-methoxyphenyl)-1-o-tolylcyclohexanol
   1-(4-chlorophenyl)-2-dimethylaminomethyl-6-(3-methoxyphenyl)-cyclohexanol
   2-dimethylaminomethyl-1-(3-fluorophenyl)-6-(3-methoxyphenyl)-cyclohexanol
   2-dimethylaminomethyl-1-(3-fluoro-4-methoxyphenyl)-6-(3-methoxyphenyl)-cyclohexanol
   1-(3-chlorobenzyl)-2-dimethylaminomethyl-6-(3-methoxyphenyl)-cyclohexanol
   2-dimethylaminomethyl-1-(3-methoxybenzyl)-6-(3-methoxyphenyl)-cyclohexanol
   1-(4-chloro-3-trifluoromethylphenyl)-2-dimethylaminomethyl-6-(3-methoxyphenyl)-cyclohexanol
   1-(3,5-dichlorobenzyl)-2-dimethylaminomethyl-6-(3-methoxyphenyl)-cyclohexanol
   2-dimethylaminomethyl-6-(3-methoxyphenyl)-1-phenylethynylcyclohexanol
   1-(4-chlorophenyl)-2-dimethylaminomethyl-6-(3-methoxyphenyl)-cyclohexanol
   2-dimethylaminomethyl-6-(3-methoxyphenyl)-1-o-tolylcyclohexanol
   1-(3-chlorobenzyl)-2-dimethylaminomethyl-6-methylcyclohexanol
   2-dimethylaminomethyl-1-(2,5-dimethylbenzyl)-6-methylcyclohexanol
   1-(2-chloro-6-fluorobenzyl)-2-dimethylaminomethyl-6-methylcyclohexanol
   1-(4-chlorobenzyl)-2-dimethylaminomethyl-6-methylcyclohexanol
   2-dimethylaminomethyl-6-methyl-1-(3-methylbenzyl)-cyclohexanol 2-dimethylaminomethyl-6-methyl-1-(3-trifluoromethylphenyl)-cyclohexanol
1-(2-chloro-3-fluorophenyl)-2-dimethylaminomethyl-6-methylcyclohexanol
2-dimethylaminomethyl-6-methyl-1-(2-methylbenzyl)-cyclohexanol
2-dimethylaminomethyl-1-(2-methoxyphenyl)-6-methylcyclohexanol
2-dimethylaminomethyl-1-(3-fluorobenzyl)-6-methylcyclohexanol
2-dimethylaminomethyl-1-(4-fluorobenzyl)-6-methylcyclohexanol
1-(2-chlorobenzyl)-2-dimethylaminomethyl-6-methylcyclohexanol
1-(3,5-dichlorophenyl)-2-dimethylaminomethyl-6-methylcyclohexanol
1-(3-chlorophenyl)-2-dimethylaminomethyl-6-methylcyclohexanol
2-dimethylaminomethyl-1-(3-fluorophenyl)-6-methylcyclohexanol
2-dimethylaminomethyl-1-(3-fluoro-4-methoxyphenyl)-6-methylcyclohexanol
2-dimethylaminomethyl-1-(4-methoxyphenyl)-6-methylcyclohexanol
2-dimethylaminomethyl-6-methyl-1-p-tolylcyclohexanol
2-dimethylaminomethyl-6-methyl-1-(3-phenylpropyl)-cyclohexanol
2-dimethylaminomethyl-1-(3-methoxyphenyl)-6-methylcyclohexanol
2-dimethylaminomethyl-6-methyl-1-thiophen-2-yl-cyclohexanol
2-dimethylaminomethyl-6-methyl-1-phenylethynylcyclohexanol
2-dimethylaminomethyl-6-methyl-1-phenethylcyclohexanol
2-dimethylaminomethyl-1-(4-fluorophenyl)-6-methylcyclohexanol
1-(3-chlorobenzyl)-2-dimethylaminomethyl-6-(3-methoxyphenyl)-cyclohexanol
2-dimethylaminomethyl-1-(4-fluoro-2-methoxyphenyl)-6-(3-methoxyphenyl)-cyclohexanol
2-dimethylaminomethyl-1-(2-methoxyphenyl)-6-(3-methoxyphenyl)-cyclohexanol
2-dimethylaminomethyl-1-(4-fluorobenzyl)-6-(3-methoxyphenyl)-cyclohexanol
1-(3-chlorophenyl)-2-dimethylaminomethyl-6-(3-methoxyphenyl)-cyclohexanol
2-dimethylaminomethyl-6-(3-methoxyphenyl)-1-p-tolyl-cyclohexanol
2-dimethylaminomethyl-6-(3-methoxyphenyl)-1-(3-phenylpropyl)-cyclohexanol
2-dimethylaminomethyl-1,6-bis-(3-methoxyphenyl)-cyclohexanol
2-dimethylaminomethyl-6-(3-methoxyphenyl)-1-thiophen-2-yl-cyclohexanol
2-dimethylaminomethyl-6-(3-methoxyphenyl)-1-phenethylcyclohexanol
3-[3-dimethylaminomethyl-2-(4-fluorophenyl)-2-hydroxycyclohexyl]-phenol
3-(3-dimethylaminomethyl-2-hydroxy-2-phenylcyclohexyl)-phenol
3-[2-(4-tert.-butylphenyl)-3-dimethylaminomethyl-2-hydroxycyclohexyl]phenol
3-(3-dimethylaminomethyl-2-hydroxy-2-vinylcyclohexyl)-phenol
1-(4-chlorophenyl)-2-dimethylaminomethyl-6-(3-methoxyphenyl)-cyclohexanol
3-dimethylaminomethyl-2-(3-methoxyphenyl)-bicyclohexyl-2-ol
2-benzyl-6-dimethylaminomethyl-1-(4-trifluoromethylphenyl)-cyclohexanol
3-(2-benzyl-6-dimethylaminomethyl-1-hydroxycyclohexyl)-phenol, and
3-(2-tert.-butyl-6-dimethylaminomethyl-1-hydroxycyclohexyl)-phenol optionally in the form of a racemate, a pure stereoisomer, an enantiomer or diastereomer, or a mixture of stereoisomers, of enantiomers or diastereomers, in an arbitrary mixture ratio; or a free acid or a free base or a physiologically acceptable salt, or a solvate or hydrate.

17. A compound according to claim 16, in the form of a hydrochloride salt.

18. A pharmaceutical composition comprising a pharmaceutically active substituted 1-aminobutan-3-ol compound according to claim 1, and at least one pharmaceutical carrier, additive or auxiliary substance.

19. A pharmaceutical composition according to claim 18, further comprising a further pharmaceutically active substance.

20. A pharmaceutical composition according to claim 18, wherein said 1-aminobutan-3-ol compound is present as a pure diastereomer, a pure enantiomer, or as a non-equimolar mixture of diastereomers or enantiomers.

21. A pharmaceutical composition according to claim 18, wherein said 1-aminobutan-3-ol compound is present as a racemate, or an equimolar mixture of diastereomers or enantiomers.

22. A method of treating pain comprising administering to a patient in need thereof an effective pain treating amount of a substituted 1-aminobutan-3-ol compound according to claim 1.

23. A method according to claim 22, wherein said pain is acute, neuropathic or chronic pain.

24. A method according to claim 22, wherein said 1-aminobutan-3-ol compound is administered as a pure diastereomer, a pure enantiomer, or as a non-equimolar mixture of diastereomers or enantiomers.

25. A method according to claim 22, wherein said 1-aminobutan-3-ol compound is administered as a racemate, or an equimolar mixture of diastereomers or enantiomers.

26. A method of treating a condition selected from the group consisting of migraines, hyperalgesia, allodynia, inflammatory pain and post-operative pain, said method comprising administering to a patient in need thereof a pharmaceutically effective amount of a substituted 1-aminobutan-3-ol compound according to claim 1.

27. A method according to claim 26, wherein said condition is selected from the group consisting of thermal hyperalgesia, mechanical hyperalgesia, allodynia, and cold-induced allodynia.

28. A method of treating a condition selected from the group consisting of epilepsy, hot flashes, post-menopausal symptoms, amyotropic lateral sclerosis (ALS), reflex sympathetic dystrophy (RSD), spastic paralysis, restless leg syndrome, acquired nystagmus, psychiatric or neuropathological disorders, painful diabetic neuropathy, symptoms and pain due to multiple sclerosis or Parkinson's disease, neurodegenerative diseases, gastrointestinal lesions, erythromelalgic or post-poliomyelitic pain, trigeminal or post-herpetic neuralgia, and convulsions, said method comprising administering to a patient in need thereof a pharmaceutically effective amount of a substituted 1-aminobutan-3-ol compound according to claim 1.

29. A method according to claim 28, wherein said condition is selected from the group consisting of bipolar disorders, anxiety, panic attacks, mood fluctuations, manic behaviour, depression, and manic-depressive behavior.

30. A method according to claim 28, wherein said condition is selected from the group consisting of Alzheimer's disease, Huntington's disease, Parkinson's disease and epilepsy.

31. A method according to claim 28, wherein said 1-aminobutan-3-ol compound is administered as a pure diastereomer, a pure enantiomer, or as a non-equimolar mixture of diastereomers or enantiomers.

32. A method according to claim 28, wherein said 1-aminobutan-3-ol compound is administered as a racemate, or an equimolar mixture of diastereomers or enantiomers.

33. A method of anticonvulsant, analgesic or anxiolytic treatment comprising administering to a patient in need thereof a pharmaceutically effective amount of substituted 1-aminobutan-3-ol compound according to claim 1.

34. A process for producing a substituted 1-aminobutan-3-ol compound according to claim 1, comprising reacting β-aminoketone corresponding to formula Ia

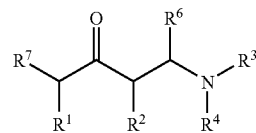

in which $R^1$ to $R^4$, $R^6$ and $R^7$ have the meanings given in claim 1, with an organometallic compound corresponding to formula III

III in which Z denotes MgCl, MgBr, MgI or Li, and $R^5$ has the meaning given in claim 1, to form a compound of formula I.

* * * * *